US006172016B1

(12) United States Patent
Pagano et al.

(10) Patent No.: US 6,172,016 B1
(45) Date of Patent: Jan. 9, 2001

(54) FRAGRANCE MATERIALS

(75) Inventors: Alex R. Pagano, Morris Township, NJ (US); Walter C. Frank, Holland, PA (US)

(73) Assignee: Bush Boakes Allen Inc., Montvale, NJ (US)

( * ) Notice: Under 35 U.S.C. 154(b), the term of this patent shall be extended for 0 days.

(21) Appl. No.: 09/351,947

(22) Filed: Jul. 12, 1999

(51) Int. Cl.[7] .......... C11D 3/50; C11D 9/44; A61K 7/46

(52) U.S. Cl. .......... 510/106; 510/108; 510/119; 510/152; 510/276; 510/367; 510/394; 424/76.1; 424/76.4; 424/401; 44/275; 512/22; 514/844

(58) Field of Search .......... 510/101, 102, 510/106, 276, 108, 119, 152, 367, 394; 512/22; 424/76.1, 76.4, 401; 44/275; 514/844

(56) References Cited

U.S. PATENT DOCUMENTS

| | | | | |
|---|---|---|---|---|
| 3,557,223 | * | 1/1971 | Rylander et al. | 568/814 |
| 4,006,218 | | 2/1977 | Sipos | 424/54 |
| 4,091,090 | | 5/1978 | Sipos | 424/45 |
| 4,313,855 | * | 2/1982 | Klein et al. | 512/2 |
| 4,701,278 | * | 10/1987 | Fehr | 510/106 |
| 4,918,052 | * | 4/1990 | Koshino et al. | 512/22 |
| 4,978,653 | * | 12/1990 | Koshino et al. | 512/21 |
| 5,087,612 | * | 2/1992 | Chapuis | 512/23 |
| 5,104,851 | * | 4/1992 | Fujikura et al. | 512/14 |
| 5,372,995 | * | 12/1994 | Sprecker et al. | 512/20 |
| 5,462,923 | | 10/1995 | Monteleone et al. | 512/19 |
| 5,552,379 | | 9/1996 | Winter et al. | 512/12 |
| 5,552,380 | | 9/1996 | Sprecker et al. | 512/20 |

FOREIGN PATENT DOCUMENTS

| | | | |
|---|---|---|---|
| 604716 | * | 9/1978 | (CH) . |
| 1240609 | * | 5/1967 | (DE) . |
| 24 44 837 | | 4/1975 | (DE) . |
| 02188549 | * | 7/1990 | (JP) . |
| 03066637 | * | 3/1991 | (JP) . |
| 07238295 | * | 9/1995 | (JP) . |
| 578300 | * | 10/1977 | (SU) . |
| 9641853 | * | 12/1996 | (WO) . |

OTHER PUBLICATIONS

Dokl. Akad. Nauk. Azerb. SSSR, vol. 22, No. 6, 1966, pp 18–22, (Translation Provided).

J. Prakt. Chem. 336, 96–109 (1994) Weyerstahl.

*Scent and Fragrances,* Günther Ohloff, Springer–Verlag, 1990, pp. 33 and 34.

Perfumes, Art, Science and Technology, edited by Müller and Lamparsky, Blackie Academic & Professional, 1994, pp. 303–306, and 318–319.

Chem. Abstracts 66, 55084y, 1966.

Levene & Marker, *J. Biol. Chem.* vol. 110, pp. 311–321 (1935).

* cited by examiner

*Primary Examiner*—Lorna M. Douyon
(74) *Attorney, Agent, or Firm*—Gibbons, Del Deo, Dolan, Griffinger & Vecchione

(57) ABSTRACT

The use of 3-methyl-5-cyclohexylpentanol, 3-methyl-5-cyclohexylpentanal or mixtures thereof as fragrance materials is disclosed. The subject materials possess unique fragrance notes and are advantageous in that they are cost-effective.

10 Claims, No Drawings

FRAGRANCE MATERIALS

This invention relates to the use of certain substituted pentane derivatives as perfumery materials.

BACKGROUND OF THE INVENTION

Many compounds have been described in the literature as fragrance materials. As is the case with many classes of compounds having varied utilities, of the many compounds that are known to possess pleasing fragrance notes, only a very small portion are utilized commercially. There are several reasons for this, notably toxicological constraints, environmental considerations, biodegradability, performance, and cost effectiveness. While all of these factors must be carefully weighed in consideration of whether to introduce a new fragrance material, perhaps the most critical are performance and cost. Performance properties include odor activity, notes, and aesthetics; substantivity; and solubility. The cost effectiveness involves manufacture costs and the amount of the compound required to impart fragrance to a consumable product. Of course, the lower the amount of fragrance material required, the higher its cost effectiveness. Many materials have met some of the above-mentioned criteria, yet have not been successful because of cost versus performance.

It must further be borne in mind that, because fragrance materials are by nature utilized in comparatively small quantities, only a very few benefit from the cost efficiency of large-scale production. All of these factors, combined with the tendency in many countries to take a more rigid regulatory position concerning ingredients in consumable products, have acted to hamper the introduction of new fragrance materials in recent years.

There is an on-going need for new fragrance materials that can be readily synthesized from relatively inexpensive raw materials, meet the criteria set forth above, possess unique fragrance notes and, perhaps most importantly, are cost-effective in use. Such materials are provided in accordance with the present invention.

SUMMARY OF THE INVENTION

The invention relates to the use of 3-methyl-5-cyclohexylpentanol, 3-methyl-5-cyclohexylpentanal and mixtures thereof as fragrance materials.

DETAILED DESCRIPTION OF THE INVENTION

The compounds found to possess attractive fragrance properties in accordance with the present invention are 3-methyl-5-cyclohexylpentanol, having the structural formula $$(C_6H_{11})\text{-}CH_2\text{-}CH_2\text{-}CH(CH_3)\text{-}CH_2\text{-}CH_2OH$$

and 3-methyl-5-cyclohexylpentanal, having the structure $$(C_6H_{11})\text{-}CH_2\text{-}CH_2\text{-}CH(CH_3)\text{-}CH_2\text{-}CHO.$$

Both of these compounds are known in the literature, but there has been to date neither recognition of their fragrant properties nor suggestion that they may possess such properties.

The preparation of 3-methyl-5-cyclohexylpentanol for a configurational relationship study was disclosed by Levene and Marker, J. Biol. Chem. Vol. 110, pages 311–321 (1935). German Offenlegungsschrift 24 44 837 (1975) discloses the preparation of 3-methyl-5-cyclohexyl pentanol, and 3-methyl-5-cyclohexylpentanal as well as intermediates in the preparation of compounds having juvenile hormone activity. Neither citation gives any indication that either of the compounds of the invention might possess fragrant properties.

3-Methyl-5-cyclohexylpentanol is conveniently prepared by hydrogenation of 3-methyl-5-phenylpentanol, a known material. Hydrogenation of phenyl rings is well known in the art and the particular method for accomplishing the above transformation is not critical. Those of ordinary skill in the art will readily appreciate that temperature, solvent, catalyst, pressure, and mixing rate, parameters that effect the hydrogenation, and how such relationships may be adjusted the relationships among them to effect the desired conversion, reaction rate, selectivity, and apparatus limitations.

The above hydrogenation is preferably carried out in a solvent at elevated temperatures and pressures over a suitable active metal hydrogenation catalyst. Acceptable solvents, catalysts, apparatus, and procedures for aromatic hydrogenation can be found in Augustine, Heterogeneous Catalysis for the Synthetic Chemist, Marcel Decker, New York, N.Y. (1996), incorporated herein by reference. Many hydrogenation catalysts are effective, including, without limitation, palladium, platinum, copper chromite, copper, rhodium, ruthenium and the supported versions thereof. Supported catalysts are preferred because the active metal is used more efficiently. Supported nickel is the preferred catalyst. Preferred supports include alumina, silica, carbon, titania, and kieselguhr, with silica and alumina being particularly preferred. While the weight percent of nickel on the support is not critical, it will be appreciated that the higher the metal weight percent the faster the reaction. Generally the nickel weight percent will range from about 5 to about 95%, preferably 25 to 75%, and most preferably 45 to 65%.

The temperature, amount of supported nickel catalyst, and hydrogenation hydrogen pressure are interrelated. The preferred temperature is from about 50° to 500° C., more preferably from about 100° to about 300° C., and most preferably from about 140° to 200° C. According to these temperature parameters, the amount of metal is preferably about 0.01 to 10 weight percent—relative to the weight of the total reaction mixture—preferably 1 to 5%, most preferably 2 to 3% by weight. The hydrogen pressure is preferably about 50 to about 5000 psi, more preferably about 100 to 1000 psi, and most preferably about 200 to 700 psi. Useful solvents include those well known in the art of hydrogenation, such as, hydrocarbons, ethers, and alcohols. Alcohols are most preferred, particularly lower alkanols such as methanol, ethanol, propanol, butanol, and pentanol. Most preferred is to use no added solvent, i.e., the substrate and product alcohols function as solvents.

3-Methyl-5-cyclohexylpentanal is likewise conveniently prepared by the oxidation of 3-methyl-5-cyclohexylpentanol by methods well known to those of skill in art. Oxidation of alcohols to aldehydes is a well known reaction. Typical reagents for effecting this transformation are pyridinium chlorochromate (available from Aldrich Chemical Co.; procedure in Tetrahedron Letters, 1975, page 2647 and Synthesis, 1982, page 245), or preferably catalytic TEMPO free radical [available from Aldrich Chemical Co.; i.e. 2,2,6,6-tetramethyl-1-piperidinyloxy, free radical] with buffered aqueous hypochlorite in the presence of potassium bromide. The procedure for this oxidation can be found in Anelli, P. et al., Org. Syn. Coll. Vol. 8, page 367 (1993). The TEMPO oxidation is preferably performed by adding 12% sodium hypochlorite (1.05 equivalents, buffered to pH 9.6 with sodium bicarbonate), to a well stirred, cooled (0° C.) solution consisting of the alcohol, 10 mole % of potassium bromide, and 1 mole % TEMPO in 5 equivalents of methylene chloride or toluene. The buffered hypochorite is added at such a rate so that the temperature of the reaction medium does not rise above 5° C. After the addition is complete, the reaction mixture is allowed to warm to room temperature and stir for fifteen minutes. The organic layer is dried, concentrated and vacuum distilled to afford the pure andehyde.

The compounds of the present invention, in contrast to the corresponding nitrile compound, i.e. 3-methyl-5-cyclohexylpentanonitrile, which is known as a citrus odorant, possess strong, fatty, rosy, waxy, muguet, carbinol, woody fragrance notes with slightly green, Phenoxanol™-like top note character. The unique fragrance notes of the subject compounds make them useful in imparting, augmenting or enhancing the olfactory component in perfume or perfume articles whether that component is intended to impart a characteristic perfume to the article or mask or modify the odor of one or more of the components thereof.

As those skilled in the art will appreciate, fragrant materials are typically utilized in combinations that may include both natural and synthetic ingredients to achieve the desired overall perfume effect. The compounds of the present invention possess unique fragrant notes and, therefore, are particularly useful individually and in such combinations in perfumes and perfumed articles, such as cosmetics, soaps, air fresheners, candles, various detergent formulations and other household products. The compounds of the invention may be utilized individually or combined in any proportion and are particularly advantageous in laundry detergent powders and liquids with or without added bleach activators, liquid and powdered cleaners containing chlorine as the active bleaching agent, acid and alkaline household cleaners, toilet soaps, fabric softeners, haircare products, such as shampoos, and air fresheners.

As is conventional in the art, the desired amount of a fragrant material to be added to a given preparation or product is determined by the nature of the product and other factors, such as whether the object is to create a particular fragrance as in a perfume or effectively mask the natural odor of other ingredients in the product to enhance acceptance by the user. The fragrant material is combined with the product in intimate admixture. Typically, where a fragrance component is a combination of a number of fragrance materials, they are combined and formulated to achieve the desired fragrant effect and then admixed with the product. The choice of a carrier, e.g. a solvent or solvent mixture, if any, to be utilized in achieving the desired intimate admixture with the final product is considered to be within the skill of the art. Although greater amounts may be utilized in certain applications, the amount of 3-methyl-5-cyclohexylpentanol, 3-methyl-5-cyclohexylpentanal or mixtures thereof in a perfume or perfumed article in accordance with the present invention will generally not exceed about 1% by weight based on the weight of the final product and can vary from about 0.01% to about 1%, preferably from about 0.05% to about 0.2% weight percent. 3-Methyl-5-cyclohexylpentanol and 3-methyl-5-cyclohexylpentanal are particularly advantageous for use as fragrant materials in such preparations because they are cost effective to produce and are projected to be biodegradable.

The following examples further illustrate the invention, but are in no way intended to be limiting thereon.

EXAMPLE 1

Preparation of 3-methyl-5-cyclohexylpentanol.

3-Methyl-5-phenylpentanol (50 g., 0.28 mol.) and 1 g. of 50% Ni on silica catalyst (2 wt %, G-49-C, United Catalyst) were stirred at 700 rpm in a Parr reactor at 180° C. and 200–600 psi of hydrogen until hydrogen absorption stopped (12 hours). The reaction mixture was filtered through a filter bed (Celite™) using toluene as a rinse solvent and concentrated to a clear, colorless liquid. The odor grade product was isolated by fractional distillation, 96% yield; bp 84–86° C. at 0.8 mm. Odor: powerful green, rosy. Mass Spectrum form 5313-24. MS (EI) m/z (relative intensity) 166 (M+–H2O, 5), 151 (M+–Me and H2O, 2).

EXAMPLE 2

Preparation of 3-methyl-5-cyclohexylpentanal.

To a cooled (0° C.) mixture of 3-methyl-5-cyclohexylpentanol (50 g, 0.27 mol), water (50 ml), potassium bromide (3.2 g), and 1 mol % TEMPO (0.4 g) in 150 ml of toluene was added aqueous sodium hypochlorite (12% available chlorine, 167 g), buffered to pH=9.6 with 2.4 g of sodium bicarbonate over a period of 30 minutes. The reaction mixture was warmed to room temperature and stirred for 15 minutes. The organic layer was separated and washed sequentially with 250 ml KI solution (4.4 g of KI, 18 ml of 36% HCl, diluted to 250 ml), 50 ml of 5% sodium thiosulfate, and 50 ml of saturated aqueous sodium chloride. The organic phase was dried with magnesium sulfate and roto-evaporated to remove the toluene. The residue was distilled at 80° C. and 0.5 mmHg to yield the product (40 g, 80% yield) as a clear liquid. MS (EI) m/z (relative intensity) 182 (M+).

We claim:

1. A method of imparting, enhancing or augmenting the fragrance of a perfume or perfumed article comprising adding thereto a fragrance-imparting amount of 3-methyl-5-cyclohexylpentanol, 3-methyl-5-cyclohexylpentanal or mixtures thereof.

2. A method in accordance with claim 1, wherein 3-methyl-5-cyclohexylpentanol is added to said perfume or perfumed article.

3. A method in accordance with claim 1, wherein 3-methyl-5-cyclohexylpentanal is added to said perfume or perfumed article.

4. A method in accordance with claim 1, wherein said article is a laundry detergent powder or liquid.

5. A perfumed article selected from the group consisting of laundry detergent powders, laundry detergent liquids, chlorine-containing powdered cleaners, chlorine-containing liquid cleaners, acid household cleaners, alkaline household cleaners, fabric softeners, shampoos, cosmetics, soaps, air fresheners and candles containing as at least a portion of its fragrant component a fragrance-imparting amount of 3-methyl-5-cyclohexylpentanol, 3-methyl-5-cyclohexylpentanal or mixtures thereof.

6. A perfumed article in accordance with claim 5, wherein said article contains a fragrance-imparting amount of 3-methyl-5-cyclohexylpentanol.

7. A perfumed article in accordance with claim 5, wherein said article contains a fragrance-imparting amount of 3-methyl-5-cyclohexylpentanal.

8. A perfumed article in accordance with claim 5, wherein said article is a laundry detergent liquid or powder.

9. A perfumed article in accordance with claim 5, wherein said article contains from about 0.01% to about 1% by weight of 3-methyl-5-cyclohexylpentanol, 3-methyl-5-cyclohexylpentanal or mixtures thereof.

10. A perfumed article in accordance with claim 9, wherein said article contains from about 0.05% to about 0.2% by weight of 3-methyl-5-cyclohexylpentanol, 3-methyl-5-cyclohexylpentanal or mixtures thereof.

* * * * *